United States Patent [19]

Waterman

[11] Patent Number: 5,795,499
[45] Date of Patent: Aug. 18, 1998

[54] STABILIZATION OF HIGH SOLIDS COATINGS WITH LIQUID COMPOSITIONS OF TRIAZINE UV ABSORBERS

[75] Inventor: Paul Sheldon Waterman, Shelton, Conn.

[73] Assignee: Cytec Technology Corp., Wilmington, Del.

[21] Appl. No.: 454,971

[22] Filed: May 31, 1995

Related U.S. Application Data

[62] Division of Ser. No. 224,204, Mar. 17, 1994, abandoned, which is a continuation of Ser. No. 486,625, Feb. 28, 1990, abandoned, which is a continuation-in-part of Ser. No. 456,917, Dec. 26, 1989, abandoned.

[51] Int. Cl.[6] .................................................. C09K 15/08
[52] U.S. Cl. ................................................................ 252/404
[58] Field of Search ............................................... 252/404

[56] References Cited

U.S. PATENT DOCUMENTS

| | | | |
|---|---|---|---|
| 2,861,105 | 11/1958 | Stanley et al. | 260/591 |
| 3,118,887 | 1/1964 | Hardy et al. | 260/248 |
| 3,244,708 | 4/1966 | Duennenberger et al. | 260/248 |
| 3,268,474 | 8/1966 | Hardy et al. | 260/45.8 |
| 3,658,910 | 4/1972 | Hechenbleikner | 260/591 |
| 3,729,442 | 4/1973 | Hechenbleikner | 260/45.95 |
| 3,843,371 | 10/1974 | Piller et al. | 96/84 |
| 4,322,212 | 3/1982 | Konrad et al. | 8/407 |
| 4,619,956 | 10/1986 | Susi | 524/87 |
| 4,740,542 | 4/1988 | Susi | 524/87 |
| 4,826,978 | 5/1989 | Migdal et al. | 544/216 |

FOREIGN PATENT DOCUMENTS

| | | |
|---|---|---|
| 2113833 | 10/1971 | Germany. |
| 1033387 | 6/1966 | United Kingdom. |

OTHER PUBLICATIONS

European Search Report —European Application No. 90125824.4.

United States Patent Appln. Serial No. 08/198,238 (filed: Feb. 18, 1994), which is a continuation of Appln. Serial No. 07/605,199 (filed: Oct. 29, 1990).

*Primary Examiner*—Kriellion S. Morgan
*Attorney, Agent, or Firm*—Bart E. Lerman; Claire M. Schultz; Michael J. Kelly

[57] ABSTRACT

Polymers are stabilized against degradation by the addition of a liquid composition comprising an organic solvent and at least 40% by weight of a triaryl triazine of the formula (I):

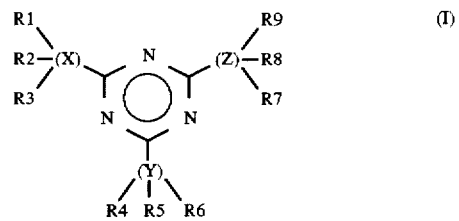

wherein X, Y, and Z are each the same or different aromatic carbocyclic radicals, and at least one of X, Y, and Z is substituted by a hydroxy group ortho to the point of attachment to the triazine ring, and at least one of R1 to R9 is an alkoxy radical of the formula, —O-(mixed alkyl) substituted at a point para to the point of attachment to the triazine ring, and the remainder of R1 to R9 are selected from the group consisting of hydrogen, hydroxy, alkyl, alkoxy, sulfonic, carboxy, halo, haloalkyl, and acylamino; with the proviso that —O-(mixed alkyl) is an alkoxy radical formed from an mixture of isomeric $C_6$ to $C_{12}$ alkyl halides containing at least 10% each of at least three different isomers.

20 Claims, 2 Drawing Sheets

STABILIZATION OF HIGH SOLIDS COATINGS WITH LIQUID COMPOSITIONS OF TRIAZINE UV ABSORBERS

This is a divisional of application Ser. No. 08/224,204, filed Mar. 17, 1994, now abandoned which is a continuation of application Ser. No. 07/486,625, filed Feb. 28, 1990, now abandoned, which is a continuation-in-part of application Ser. No. 07/456,917, filed Dec. 26, 1989, now abandoned.

FIELD OF THE INVENTION

This invention relates to stabilization of polymers with liquid compositions containing highly soluble triazine ultraviolet absorbers (UVA).

BACKGROUND OF THE INVENTION

The use of triazine-type UVAs by themselves or in combination with HALS to stabilize plastics and coatings against light-induced degradation is well known.

U.S. Pat. Nos. 3,118,887 and 3,268,474 disclose the stabilization of plastic and resinous compositions against the effects of ultraviolet light by incorporating therein one or more triaryl triazines. It is further taught that at least one of the aryl groups is substituted by a hydroxyl group ortho to the point of attachment of the aryl group to the triazine nucleus.

U.S. Pat. Nos. 4,619,956 and 4,740,542 disclose a method of stabilizing a polymer film, coating, or a molded article against the action of light, moisture, or oxygen. This method incorporates in a polymer a stabilizingly effective amount of a 2,2,6,6-tetraalkylpiperidine compound hindered amine light stabilizer (HALS) or salts or complexes thereof, together with a tris-aryl-s-triazine compound (UVA). Triazines taught to be particularly effective are those in which at least one aryl group was substituted with (i) a hydroxyl group ortho to the point of attachment of the aryl group to the triazine nucleus, and (ii) an alkoxy group —(OR) which is para to the point of attachment of the aryl group to the triazine nucleus.

Despite good performance of UVAs or UVA/HALS combinations there are limits to the usefulness of these stabilizer ingredients due to physical properties such as UVA solubility. For example, 2,4,6-tris-s-triazines having octyl and hydroxyl substituents are relatively high melting solids with low solubilities in organic solvents such as xylene and butyl acetate. Consequently, the manner in which such triazines can be employed in the coatings industry is restricted to (i) direct addition of solid UVA to a polymer, or, (ii) addition as a relatively dilute (less than 30 weight percent concentration) of UVA in an organic solvent.

The direct addition of a solid stabilizer to a polymer is often not practical on an industrial scale. For example, caking may become a serious problem, the mixture may require additional heating and stirring to become homogeneous, dissolving the solid may require long periods of time, or dissolution may be incomplete. Moreover, problems of incompatibility between polymer and stabilizer can appear as "blooming" or exudation of stabilizer in the finished polymer product. All of these factors affect the overall quality of the stabilized polymer product.

A second method of stabilizer addition to polymers is to add the stabilizer as a solution. Typically, the stabilizer is added as a solute dissolved in a suitable organic solvent. The disadvantage of this method in the case of low solubility triazine UVAs is that it permits addition of only relatively small amounts of stabilizer, together with excess solvent. Excessive solvent volumes become a problem in coatings and plastics manufacturing and result in a buildup of unwanted volatile organic components ("VOC") in the polymer product.

Stabilizer systems disclosed in prior art have attempted to address some of the unsatisfactory aspects mentioned above, however, the prior art approaches to these problems have not been entirely satisfactory. For example, U.S. Pat. Nos. 3,658,910 and 3,729,442 disclose an improved benzophenone-type ultraviolet absorber, 4-alkoxy-2-hydroxybenzophenone. Improvement is obtained by modifying the alkyl group from normal octyl, which gives a solid benzophenone-type stabilizer as disclosed in U.S. Pat. No. 2,861,105 and German offenlegungschrift 1,806,870, to an isomeric mixture of octyl referred to as "Oxo" octyl which gives a liquid benzophenone-type stabilizer as disclosed in U.S. Pat. Nos. 3,658,910 and 3,729,442. Although the liquid form benzophenone has superior performance when compared to its solid form, the entire class of benzophenone-type stabilizers are inferior in performance to other classes of UV-absorbers such as triazines. Benzophenone-type stabilizers further suffer from high volatility which makes them unsuited for high temperature bake coatings applications, in particular, automotive coatings applications.

The UVA deficiencies of the benzophenone-type absorbers in areas such as volatility and performance, and the deficiency of the triazine-type absorbers in the area of solubility could be overcome if an improved triazine-type ultraviolet absorber of higher solubility is found. In particular, it would be a welcome contribution to the art of polymer stabilization if triaryl triazines UVAs of high solubility in common solvents were made available.

SUMMARY OF THE INVENTION

This invention is a method of making highly organic solvent soluble triaryl triazine UVAs useful for the stabilization of plastics. These highly soluble triaryl triazine UVAs are prepared by alkylating polyhydroxy triaryl triazines with an isomeric mixture of an alkyl halide.

This invention is also a highly organic solvent soluble triaryl triazine produced by the novel process of the invention.

This invention is also a polymer stabilizing composition comprising the novel triaryl triazines dissolved at high concentration in an organic solvent.

This invention is also a method of stabilizing polymers by incorporating into said polymers the highly organic solvent soluble triaryl triazine UVA of this invention.

This invention is also a stabilized film, or coating, or article formed by coating a substrate with stabilized polymers produced by the stabilizing method of this invention.

DETAILED DESCRIPTION OF THE INVENTION

Figure 1:
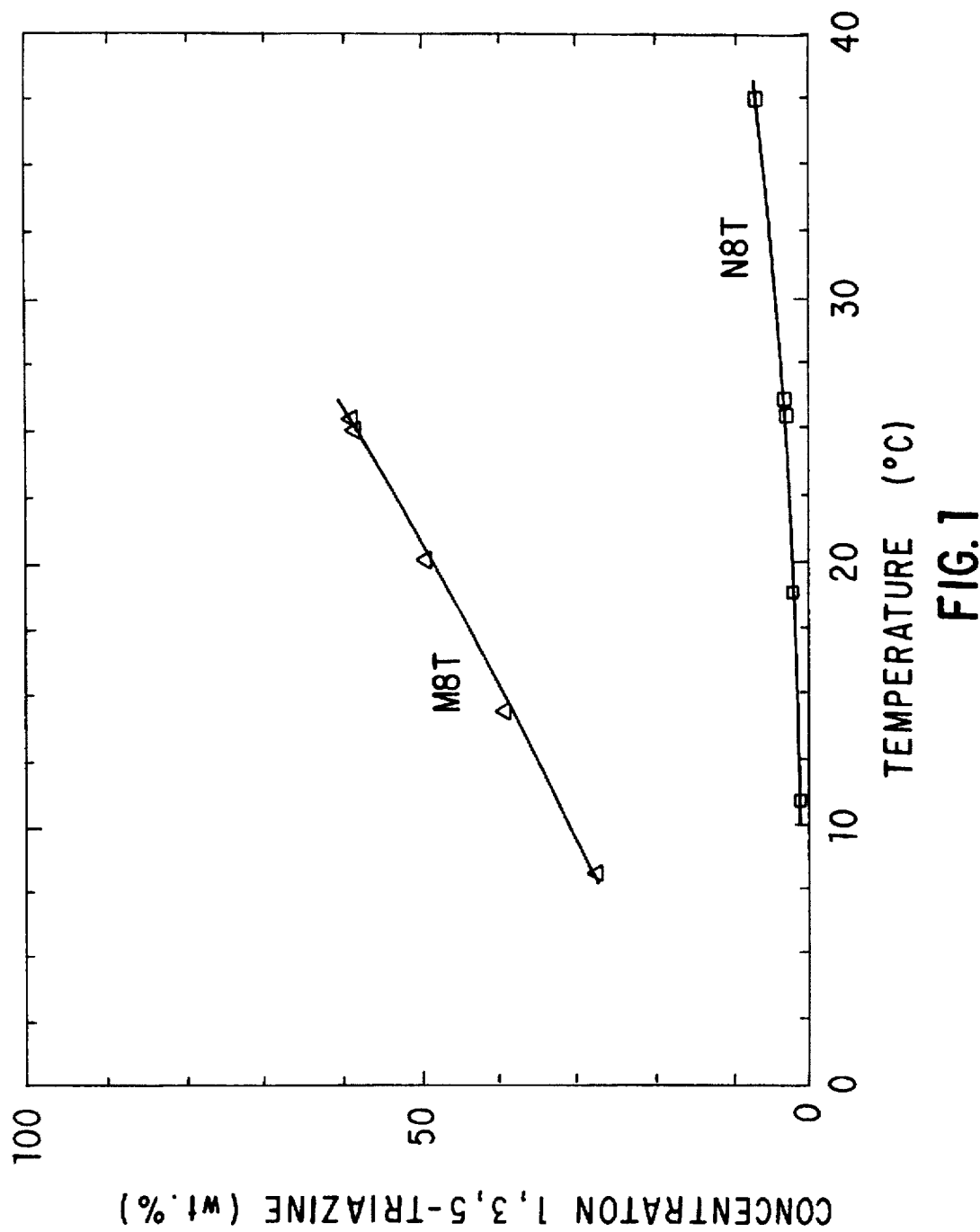
FIG. 1 shows solubility temperature curves of 2,4-di-(2,4-dimethylphenyl)-6-(2-hydroxy-4-O(mixed octoxy)phenyl)-1,3,5-triazine (coded, "M8T) and 2,4-di-(2,4-dimethylphenyl)-6-(2-hydroxy-4-O-normal oxtoxy-phenyl)-1,3,5-triazine (coded "N8T") in butyl acetate solvent.

The novel triaryl triazine compounds of this invention are represented by the formula (I) below:

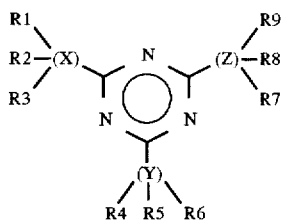

wherein X, Y, and Z are each the same or different aromatic carbocyclic radicals, and at least one of X, Y, and Z is substituted by a hydroxy group ortho to the point of attachment to the triazine ring, and at least one of R1 to R9 is an alkoxy radical of the formula, —O-(mixed alkyl) substituted at a point para to the point of attachment to the triazine ring, and the remainder of R1 to R9 are selected from the group consisting of hydrogen, hydroxy, alkyl, alkoxy, sulfonic, carboxy, halo, haloalkyl, and acylamino.

The symbol, "—O-(mixed alkyl)" as used herein is an alkoxy radical formed from a mixture of isomeric C6 to C12 alkyl halides containing at least 10 weight percent of at least three different isomers. Preferably, the "—O-(mixed alkyl)" group is predominantly a mixture of alkyl isomers having the same number of carbon atoms. For example, the —O-(mixed alkyl) group may be a mixture of eight carbon atom alkyl isomers wherein at least three different octyl isomers are present.

Preferred triaryl triazine compounds of this invention are represented by the formula (I), wherein X, Y, and Z are each phenyl radicals and only one of X, Y, or Z is substituted by a hydroxyl group in the ortho position, an alkoxy group of the formula —O-(mixed alkyl) is substituted on the same phenyl radical as the hydroxyl group at a point para to the point of attachment of the phenyl radical to the triazine ring, and the remainder of R1 to R9 are selected from the group consisting of hydrogen, one to twelve carbon atom alkyl, and —O-(mixed alkyl) groups.

An illustrative triaryl triazine is 2,4-di-(2,4-dimethylphenyl)-6-(2-hydroxy-4-O-(mixed alkyl))phenyl)-1,3,5-triazine.

I. A PROCESS FOR PREPARING NOVEL TRIARYL TRIAZINES

General methods for preparing triaryl triazines have been disclosed in U.S. Pat. Nos. 3,118,887 and 3,268,474, the disclosures of which are incorporated herein by reference. However, the prior art does not teach alkylation products of hydroxyaryl triazines with mixed isomer alkyl halides to produce the novel highly soluble triaryl triazines of this invention.

The process for preparing the novel highly soluble triazines is by alkylating with mixed isomeric alkyl halides a polyhydroxy triaryl triazine represented by the formula (II) below:

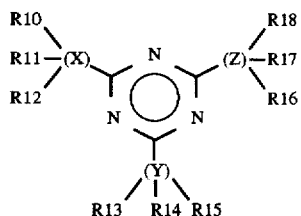

wherein X, Y, and Z are each the same or different aromatic carbocyclic radicals, and at least one of X, Y, and Z has two hydroxy groups having positions, respectively, ortho and para to the point of attachment to the triazine ring, and the remainder of R10 to R18 are selected from hydrogen, hydroxy, alkyl, alkoxy, sulfonic, carboxy, halo, haloalkyl, and acylamino.

Preferred triaryl triazine reactants suitable for alkylation with mixed isomeric alkyl halides are represented by the formula (III) below:

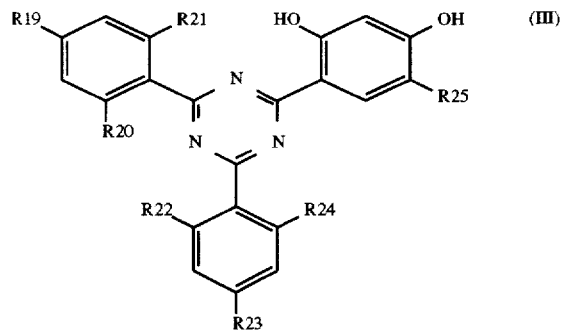

wherein R19, R20, R21, R22, R23, R24, and R25 are selected from the group consisting of hydrogen and one to twelve carbon atom alkyl groups.

A preferred process of the invention is to monoalkylate the triazine of formula (III) with an isomeric mixed alkyl halide. It is particularly preferred to use an isomeric mixture of eight carbon alkyl halides as the alkylating agent.

The triaryl triazine UVAs of the invention may also be substituted by ortho-hydroxy groups on 2 or 3 of the aromatic carbocyclic rings attached to the triazine nucleus. However, these poly-ortho-hydroxy type triazines, although effective as ultraviolet absorbers, are generally more highly colored than mono-ortho-hydroxy type triazines. Consequently, the mono-ortho-hydroxy triazines prepared from triaryl triazines of formula (III) are generally preferred for stabilization of coatings.

An illustration of a specific triaryl triazine reactant useful for practicing the method of this invention is 2-(2,4-dihydroxyphenyl)4,6-bis-(2,4-dimethylphenyl)-1,3-5-triazine.

The mixed isomeric alkyl halides suitable for practicing the method of the invention are generally chlorides, bromides, or iodides, with chlorides being preferred because of cost and availability.

The alkyl radicals of the mixed isomeric alkyl halide reactant may contain a wide variety of isomers having a range of from six to twelve carbon atoms. It is a preferred practice of this invention that the alkyl radicals of the alkyl halide be predominantly (over 90 weight percent) a mixture of isomers of one given carbon atom chain length, for example, a mixture of eight carbon atom isomers. It is also within the preferred practice of this invention to combine isomer mixtures, that is, to use an alkyl halide ingredient wherein, for example, one-third of the alkyl groups are derived from six carbon atom mixed isomers, one-third of the alkyl groups are derived from eight carbon atom mixed isomers, and one-third of the alkyl groups are derived from ten carbon atom mixed isomers.

The alkyl halide reactant predominantly reacts with the hydroxyl group in the para positions in formulae (II) and (III). The para hydroxyl group is more reactive than the ortho position hydroxyl and its predominant reaction is accomplished by using no more than about a 10% stoichiometric excess of mixed isomer alkyl halide reactant per mole of para hydroxyl group on the triazine reactant. Other reaction conditions which favor predominant reaction of the para hydroxyl group are (i) use of a catalyst, and (ii) use of reaction temperatures below 200° C.

A particularly preferred source of mixed isomer $C_6$ to $C_{12}$ alkyl groups for the mixed isomer alkyl chloride reactant are "Oxo" process alcohols. The "Oxo" process and products are well known and are described in detail in the Kirk-Othmer "Encyclopedia of Chemical Technology", 2nd Edition, Volume 14, page 373 to page 390.

The products derived from the 'Oxo Process' are further described in U.S. Pat. No. 3,658,910 (column 1, line 54 to column 2, line 27) as follows:

R is a mixture of random branched alkyl groups having 6 to 10 carbon atoms and are of the 'Oxo' type ... A typical commercially available isooctanol has the analysis 3,4-dimethyl-1-hexanol 20%, 3,5-dimethyl-1-hexanol 30%, 4,5-dimethyl-1-hexanol 30%, 3-methyl-1-heptanol and 5-methyl-1-heptanol together 15% and unidentified alcohol 5%. A typical commercially available isodecanol is a mixture of a plurality of primary saturated alcohols having ten carbon atoms. There is a major proportion of a mixture of trimethyl heptanols and small amounts of other isomeric primary saturated decanols. ... In general such mixtures contain at least 10% of at least three different branched chain isomers.

Solubility Properties of the Tris-Aryl Triazines:

It is the discovery of this invention that the triaryl triazines of Formula (I) although solids have unexpectedly superior solubility properties not found or suggested in the prior art. For example, U.S. Pat. Nos. 3,729,442 and 3,658,910 teach that when the normal octyl group in benzophenone-type UV absorbers is replaced with an isomeric mixture of $C_6$ to $C_{12}$ alkyl group, the solid benzophenone derivative is converted to a liquid derivative. It is a discovery of this invention that when a non-benzophenone-type UVA, specifically a triaryl triazine, is reacted with an isomeric mixed alkyl halide derived from an isomeric alcohol that a solid results, and that this solid unexpectedly has significantly improved solubility in compositions useful for polymer stabilization.

The increased solubility of the triazines of this invention gives rise to two important advantages not present in the methods of stabilization in prior art, namely;

a. Low Volatile Organic Components (VOC), which is the direct result of the increased solubility of the triazines of this invention, and b. Increased compatibility with coatings and plastics to which the triazines of this invention are added.

Without being bound by any theory of operation it is believed that the triaryl triazines produced by alkylating the triaryl triazines of formulae (II) and (III) gives an isomeric mixture having unexpectedly enhanced solubility properties. This enhanced solubility is conceivably related to enhanced compatibility of the triaryl triazines of this invention in polymer systems, and includes such possible advantages as resistance to "blooming", stabilizer exudation, and etc.

II. A POLYMER STABILIZING COMPOSITION

The triaryl triazine UV absorbers of this invention are characterized as being highly soluble in organic solvents. For the purpose of this invention high organic solvent solubility is defined as the triaryl triazines of formula (I) having a solubility of at least 40 weight percent in xylene at 25 degrees C. (based on the total weight of solution). The triazines of the invention are typically dissolved in a solvent with agitation with or without the aid of heat. It is preferred to prepare solutions of novel triazines having a concentration of from 40 weight percent up to the solubility limit of the triazines. Typically, triazine concentrations of from 50 to 80 weight percent are preferred for commercial applications.

The polymer stabilizing composition comprises as its essential component ingredients the following:

A. an organic solvent,

B. a triaryl triazine compound represented by formula (I), supra.

Preferably the —O-(mixed alkyl) group(s) in the triaryl triazine is derived from a mixture of isomers containing at least 10% of at least three different branched $C_6$ to $C_{12}$ alkyl isomers as previously stated in the definition of Formula (I). It is particularly desired that the alkyl isomer mixture be derived from the "Oxo" process alcohols.

The Liquid Organic Solvent Component:

The solvent ingredient of the composition is not critical and may be selected from a wide variety of liquid organic solvents known to have utility and compatibility in polymer formulations. Suitable solvents are liquid at ambient temperatures and are non-reactive with polymers, triazine-type ultraviolet light absorbers, and other optional components. Illustrative classes of solvents are alkanes, halogenated alkanes, aromatic hydrocarbons, halogenated aromatic hydrocarbons, alcohols, aldehydes, esters, ethers, and ketones. Examples of specific compounds useful as solvents in the process of the invention are xylene and butyl acetate. The utility of any proposed solvent may be easily determined by testing the solubility of the triaryl triazine of the invention at ambient temperatures.

It is also possible to use as the solvent ingredient of the composition a solvent used as reaction media for the preparation of the mixed isomer triaryl triazines of this invention. Alternatively, it is useful to employ solvents in the purification step of the triazine synthesis as the selected organic solvent ingredient of the stabilizing composition of the invention.

Optional Stabilizer Composition Ingredients:

The stabilizing composition may contain other ingredients in addition to the solvent and triaryl triazine of the invention. For example, the stabilizing composition may contain a minor proportion of byproducts from the alkylation process used to prepare the triazine, if such byproducts are not detrimental to the polymer being stabilized.

The polymer stabilizing composition of the invention may contain, if desired, only triaryl triazines of formula (I), together with a solvent. Alternatively, the stabilizing composition may contain a variety of other ingredients known to be useful in polymer formulations. Such optional ingredients include other UVA stabilizers, antioxidants, and/or hindered amine light stabilizers (HALS). It may be desirable to use the UVAs of this invention in combination with HALS, much in the same manner as low organic solvent soluble triaryl triazines have been used in combination with HALS in the prior art (see, for example, U.S. Pat. No. 4,619,956).

A preferred class of optional HALS ingredients having utility in preparing the plastic stabilizing compositions of this invention are broadly described as 2,2,6,6-tetraalkylpiperidine hindered amine type light stabilizer including their N-oxides, N-hydroxides, and N-alkoxides, or their acid addition salts or complexes with metal compounds thereof. Such 2,2,6,6-tetraalkylpiperidine hindered amine type light stabilizers are described in U.S. Pat. Nos. 4,356,307 4,778,837, 4,740,542, and 4,619,956 the disclosures of which are incorporated herein by reference.

Also suitable as HALS for use in the composition and method of the invention are polymeric compounds of which the recurring structural unit contains polyalkylpiperidine radicals, especially polyester, polyethers, polyamides, polyamines, polyurethanes, polyureas, polyaminotriazines, and copolymers thereof which contain such radicals.

Useful polyalkylpiperidine derivatives also include basic compounds that can form salts with acids. Examples of suitable acids for such salt formation include but are not limited to inorganic and organic acids such as, carboxylic, sulfonic, phosphonic, phosphinic, hydrochloric, boric, phosphoric, acetic, salicylic, toluenesulfonic, and benzenephosphonic.

III. A METHOD OF STABILIZING POLYMERS

This invention includes an improved method of stabilizing a polymer against the action of light, moisture, and oxygen by incorporating into the polymer a stabilizingly effective amount of the mixed isomer triaryl triazines previously represented by formula (I).

The mixed isomer triaryl triazines are most conveniently incorporated into the polymer by mixing into a polymer containing liquid the concentrated liquid stabilizer composition of the invention comprising an organic solvent having dissolved therein the mixed isomer triaryl triazines of the invention. Liquid additives are particularly convenient for processing since they are easily measured, transported, and uniformly dispersed into the polymer to be stabilized. Alternatively, the triaryl triazines of formula (I) may be added to unstabilized polymer as a solid, but this method of addition is not the preferred practice of this invention because of the difficulty of uniform addition.

Many types of polymers may be stabilized by the method of the invention. Such polymers include acrylics, alkyds, polyesters, polyurethanes, polysiloxanes, polyolefins, polycarbonates, polyamides, polyvinyl halides, styrenics, and epoxies.

The stabilization method is typically practiced by incorporating the triaryl triazine ingredient into the polymer in amounts of from about 0.01 to about 5 wt % based on the weight of total polymer in the composition. In those instances where a HALS is additionally used said HALS is also incorporated into the polymer in amounts of from about 0.01 to about 5 wt % based on the weight of total polymer in the composition.

In addition to the incorporation of the triaryl triazines into the polymers either alone or optionally with HALS, other known stabilizers and co-stabilizers can also be used. These stabilizers can be, for example:

1. Antioxidants which are alkylated phenols, alkylated hydroquinones, hydroxylated thiophenyl ethers, alkylidene-bisphenols, acylaminophenols, esters of beta-(3,5-di-tert-butyl-4-hydroxyphenyl) propionic acid with monohydric or polyhydric alcohols, and amides of beta-(3,5-di-tert-butyl-4-hydroxyphenyl) propionic acid;
2. Other ultraviolet light stabilizers;
3. Metal deactivators;
4. Phosphites and phosphines;
5. Compounds which decompose peroxides;
6. Nucleating agents;
7. Fillers; and
8. Other additives, for example, plasticizers, lubricants, emulsifiers, pigments, fluorescent whitening agents, flameproofing agents, antistatic agents and blowing agents.

The polymers which can be stabilized according to the method of this invention include those which form films and coatings, and those from which molded articles are produced. Preferably acid catalyzed thermoset acrylic or alkyd coatings are stabilized, most preferably high solids thermoset acrylic coatings are stabilized by the method of this invention.

IV. COATED ARTICLE AND METHOD OF MAKING

This invention is an improved method of making a coated article by applying to a substrate a polymer stabilized with the novel triaryl triazines of this invention.

The stabilized polymer may be in the form of a solution, dispersion, emulsion, invert emulsion, or hot melt and is applied by any conventional process such as padding, dipping, brushing, and spraying.

The substrate receiving the stabilized polymer to form a coated article may be metallic or non-metallic, for example, aluminum, steel, glass, or plastic.

After applying the polymer to the substrate the coating may be cured (if crosslinkable), usually by application of heat to form a coated article.

The use of saturated or nearly saturated solutions of concentrated stabilizing composition (comprising solvent and novel triazine) is preferred since less solvent (and consequently lower level of volatile organic components) will be introduced into a polymer, coating or film to be stabilized.

The following examples are provided for the purpose of illustration only and should not be construed as limiting the invention in any way as variations of the invention are possible which do not depart from the scope of the appended claims.

EXAMPLE 1

A mixture of 2,4-di-(2,4-dimethylphenyl)-6-(2,4-dihydroxyphenyl)-1,3,5-triazine (40 g), mixed isomeric octyl chlorides, analysis 95% $C_8$, (16 g), potassium iodide (0.7 g), PEG 400® (polyethylene glycol, molecular weight 380–420, available from Aldrich Chemicals, Milwaukee, Wis.) (4 g), sodium hydroxide (4 g) dissolved in methyl isobutyl ketone was heated under reflux (122° C.) for 16 hours. After cooling to 80° C., the reaction mixture was acidified with dilute hydrochloric acid, and the resulting aqueous layer was removed. The organic layer was washed twice with warm water (75 ml for each washing) and the volatiles were removed in vacuo under reduced pressure. The residue (45 g) was dissolved in xylene (10 g) and decolorized with activated charcoal and filtered to give 2,4-di-(2,4-di-methylphenyl)-6-(2-hydroxy-4-O-(mixed alkyl)phenyl)-1,3,5-triazine; (where "mixed alkyl" was an isomeric mixture of $C_8$ alkyl groups) as an amber solution (50 g).

This example illustrates the preparation of a concentrated solution, in xylene, of an isomeric $C_8$ mixture alkyl groups in 2,4-di-(2,4-dimethylphenyl)-6-(2-hydroxy-4-O-(mixed alkyl)phenyl)-1,3,5-triazine. The reaction product is an ultraviolet light stabilizer product of this invention prepared according to the alkylation process of this invention.

EXAMPLE 2

The product of Example 1 was heated to 90° C. under vacuum at 50 mm of mercury until all volatiles were removed. The residue was the triazine of formula (I) with an isomeric mixture of $C_8$ alkyl groups containing 2,4-di-(2,4-dimethylphenyl)-6-(2-hydroxy-4-O-(mixed alkoxy)phenyl)-1,3,5-triazine as a viscous oil which solidified within one month standing at room temperature.

This example illustrates the preparation of 2,4-di-(2,4-dimethylphenyl)-6-(2-hydroxy-4-O-(mixed alkyl) phenyl)-1,3,5-triazine (where "mixed alkyl" is an isomeric mixture of $C_8$ alkyl groups) as a solid product.

EXAMPLE 3

Figure 2:
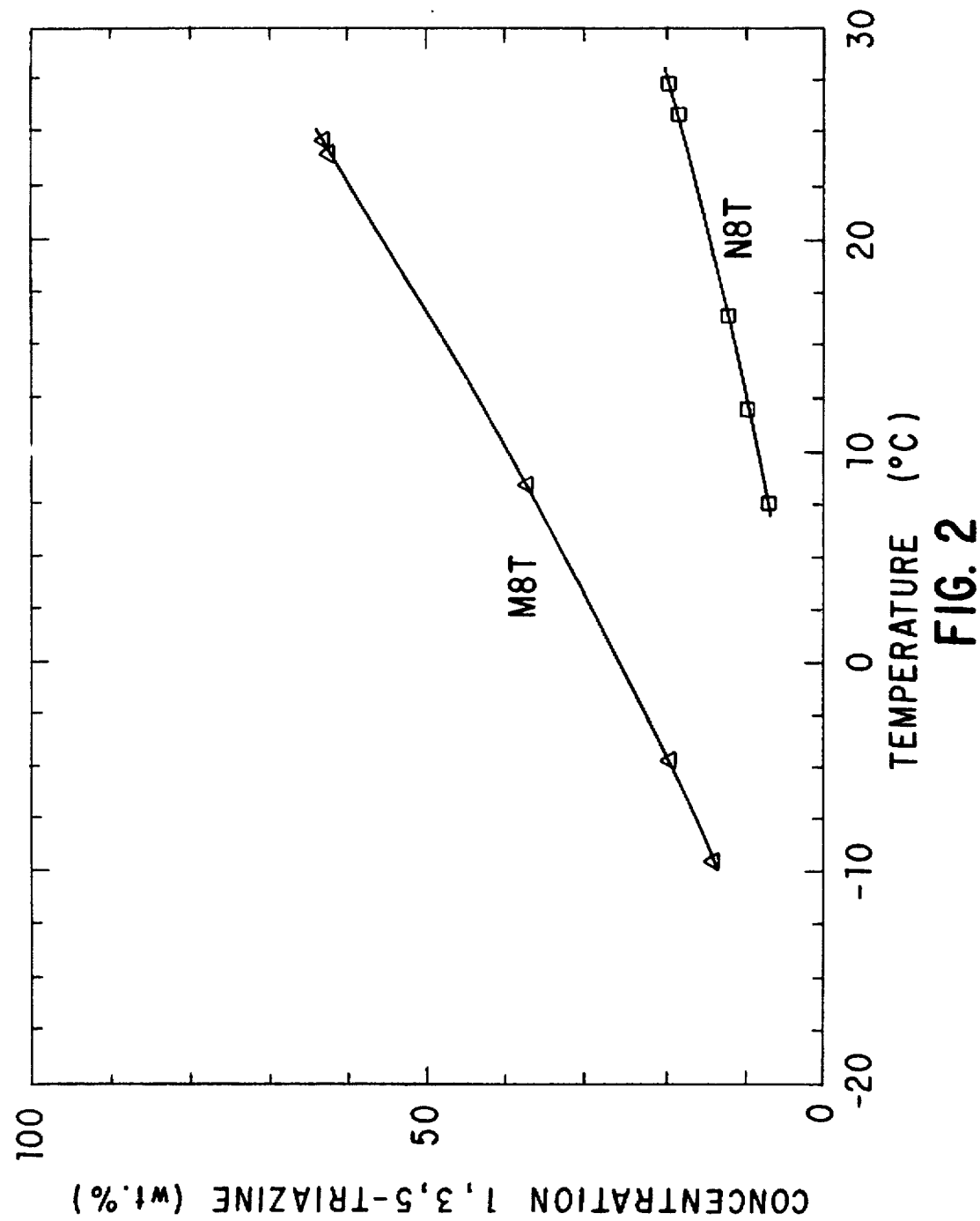
FIG. 2 shows solubiltiy temperautre curves of M8T and N8T in xylene.

The solubility of the M8T and the prior art N8T in both xylene and butyl acetate solvents for temperatures in the range from −20° C. to 30° C. was determined using a method where a suspension of known concentration was adjusted until the solute just dissolved. The sample temperatures were measured to ±0.1° C. and regulated to ±0.1° C. in a constant temperature bath. The results of the solubility tests are shown in the following Tables 1A and 1B and in FIGS. 1 and 2.

TABLE 1A

| M8T Xylene | | N8T Xylene | |
|---|---|---|---|
| Temp. °C. | wt. % | Temp. °C. | wt. % |
| −9.5 | 14.4 | 7.6 | 6.9 |
| −4.6 | 19.7 | 12.0 | 9.7 |
| 8.5 | 37.4 | 16.4 | 12.3 |
| 24.1 | 62.6 | 25.9 | 18.2 |
| 24.8 | 63.2 | 27.3 | 19.7 |

TABLE 1B

| M8T Butyl Acetate | | N8T Butyl Acetate | |
|---|---|---|---|
| Temp. °C. | wt. % | Temp. °C. | wt. % |
| 8.2 | 27.8 | 10.9 | 1.1 |
| 14.4 | 39.5 | 18.8 | 1.9 |
| 20.1 | 49.8 | 25.5 | 2.9 |
| 25.0 | 58.5 | 26.1 | 3.1 |
| 25.5 | 59.2 | 37.4 | 6.5 |

An additional experiment was performed to compare the M8T and N8T stabilizer solubilities at approximately the same temperature (25° C.). In addition, the calculated theoretical solubility of each compound at 25° C. was determined based on the solubility curve data described in this Example and displayed in FIGS. 1 and 2. The results of these determinations are shown in Table 1C below:

TABLE 1C

| Solute | Solvent | Experiment Temp. °C. | Solubility Conc. (actual) | Solubility Conc. 25° C. (Calculated) |
|---|---|---|---|---|
| M8T | Xylene | 24.8 | 63.2 | 63.5 |
| M8T | BA | 25.0 | 58.5 | 58.3 |
| N8T | Xylene | 25.4 | 17.8 | 17.9 |
| N8T | BA | 25.5 | 2.94 | 2.92 |

BA is butyl acetate

This example illustrates the much higher solubility, in organic coatings solvents, of triaryl triazines which are a product of the invention containing an isomeric mixture of $C_8$-O-(mixed alkyl) groups compared to a similar triaryl triazine prepared with normal octyl halide (non-isomeric) which is a product outside the scope of this invention.

EXAMPLE 4

1. Test Procedure

The effectiveness of the light stabilizer systems of the following Examples was determined by measuring the gloss retention (ASTM Test Procedure D523) and yellowness index (ASTM Test Procedure D1925) of a coating after exposure in an accelerated weathering unit such as the QUV (ASTM Test Procedure G53).

2. Basic Clear Coating Formulations 13.0 parts ACRYLOID® AT-400 brand of thermosetting acrylic resin (a trademark of Rohm & Haas Co.) (75% solids); 5.25 parts CYMEL® 303 brand of melamine resin (a trademark of American Cyanamid Co.); 0.15 parts CYCAT® 4040 brand of toluenesulfonic acid catalyst (a trademark of American Cyanamid Co.) (40% in isopropanol); 3.3 parts xylene; and 3.3 parts butanol.

3. Coatings Formulations with Stabilizer.

Three acrylic coating formulations were prepared by adding a hindered amine light stabilizer (HALS) and an ultraviolet absorber (UVA) as follows:

Formulation A

Formulation A was prepared by adding solid 2,4-di-(2,4-dimethylphenyl)-6-(2-hydroxy-4-n-octoxy-phenyl)-1,3,5-triazine (n-octyl triazine) at 2 wt % level based on total resin solids, and by adding the hindered amine light stabilizer of formula (IV);

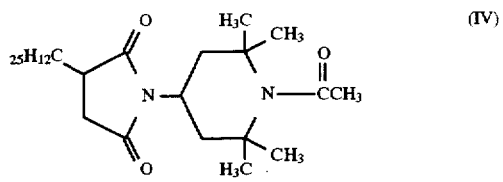

at 1 wt % level based on total resin solids, to the basic clear coating formulation of Example 4, part 2.

Formulation B

Formulation B was prepared by adding the solid product of Example 2 at 2 wt % level based on total resin solids and by adding the hindered amine light stabilizer of formula (IV) at a 1 wt % level based on total resin solids, to the basic clear coating formulation of Example 4, part 2.

Formulation C

Formulation C was prepared by adding SANDUVOR® 3206 ultraviolet absorber (represented by formula V),

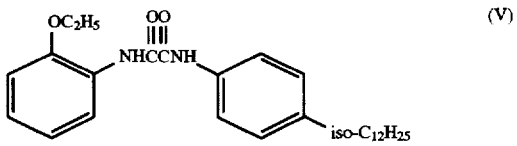

a product of Sandoz Chemicals Corporation, Charlotte, N.C., at 2 wt % level based on total resin solids, and by adding TINUVIN®, 440 hindered amine light stabilizer (represented by formula VI),

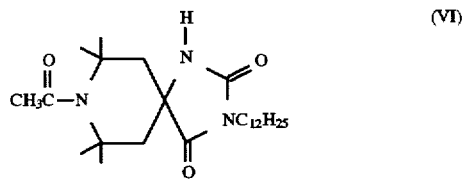

a product of Ciba-Geigy Corporation, Hawthorne, N.Y., at 1 wt % level based on total resin solids, to the basic clear coating formulation of Example 4, part 2.

4. Measurement of Stabilizing Effectiveness

BONDERITE® 40 brand of cold rolled steel test panels, coated with a primer and a white base coat based on a thermosetting acrylic resin were coated with the clear resin formulation described above (containing the stabilizer to be evaluated) and cured for 30 min. at 120° C. Clear coating thickness was about 2 mils (0.0508 mm). The coated test panels were subjected to weathering in a QUV tester. In this test, the samples were subjected to alternate cycles of UV light at 70° C. for 8 hours and a humid atmosphere with no UV light at 50° C. for 4 hours. Subsequently, the gloss was measured. The gloss retention of the cured coatings A, B and C, obtained by curing the formulations A, B and C of Example 4, part 3, are summarized in Table 2.

TABLE 2

Gloss Retention of Cured Thermosetting Acrylic Coatings Stabilized with Stabilizer Combinations

| | % Gloss (20°) After Exposure (QUV) | | |
|---|---|---|---|
| | 2400 Hours | 3200 Hours | 4000 Hours |
| Coating A | 98 | 97 | 94 |
| 2% n-octyl triazine 1% HALS Coating B | 99 | 99 | 93 |
| 2% Example 1 product 1% HALS Coating C | 92 | 57 | 33 |
| 2% SANDUVOR 3206 1% TINUVIN 440 | | | |

It is concluded from the results in Table 2 that the combination of an ultraviolet absorber (UVA) of this invention (viz., the product of Example 1) with a hindered amine light stabilizer (HALS) gives an effective stabilizer system that compares favorably with commercial stabilizer systems such as the combination of SANDUVOR®, 3206 and TINUVIN® 440. Moreover, the highly organic solvent soluble triazines of this invention compare favorably with systems using a HALS together with normal octyl triazine ultraviolet absorber.

Although the present invention has been described with reference to certain preferred embodiments, it is apparent that modifications and changes may be made therein by those skilled in the art without departing from the scope of this invention as defined in by the appended claims.

I claim:

1. A triaryl triazine ultraviolet light stabilizer composition comprising a mixture of compounds represented by the formula below:

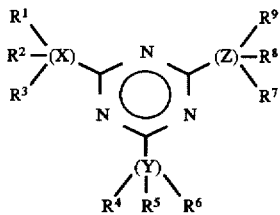

wherein independently for each of said compounds

X, Y, and Z are each the same or different aromatic carbocyclic radicals, and at least one of X, Y, and Z is substituted by a hydroxy group ortho to the point of attachment to the triazine ring, and at least one of $R^1$ to $R^9$ is an alkoxy radical of the formula —O-($C_6$ to $C_{12}$ alkyl) substituted at a point para to the point of attachment to the triazine ring, and the remainder of $R^1$ to $R^9$ are selected from the group consisting of hydrogen, hydroxy, alkyl, alkoxy, sulfonic, carboxy, halo, haloalkyl, and acylamino;

with the proviso that in said mixture are present at least 10% each of at least three different isomers of said —O-($C_6$ to $C_{12}$ alkyl) radical, wherein % is based on the total —O-($C_6$ to $C_{12}$ alkyl) radicals.

2. The triaryl triazine ultraviolet light stabilizer composition of claim 1 wherein for each said triaryl triazine compound:

(a) X, Y, and Z are each phenyl groups, (b) only one of X, Y, and Z is substituted by a hydroxy group ortho to the point of attachment to the triazine ring, (c) at least one —O-($C_6$ to $C_{12}$ alkyl) radical is substituted, on the same phenyl group as said hydroxy group, at a point para to the point of attachment of the phenyl group to the triazine ring, and (d) the remainder of the $R^1$, $R^2$, $R^3$, $R^4$, $R^5$, $R^6$, $R^7$, $R^8$, and $R^9$ are selected from the group consisting of hydrogen and alkyl groups.

3. The triaryl triazine ultraviolet light stabilizer composition of claim 1 wherein said at least three different —O-($C_6$ to $C_{12}$ alkyl) radicals are formed from a mixture of isomeric $C_6$ to $C_{12}$ alkyl halides containing at least 10% each of at least three different isomers.

4. The triaryl triazine ultraviolet light stabilizer composition of claim 3 wherein said at least three different-O-($C_6$ to $C_{12}$ alkyl radicals are formed from a mixed isomeric alkyl halide derived from "Oxo" process alcohols.

5. The triaryl triazine ultraviolet light stabilizer composition of claim 3 wherein the alkyl group of said alkyl halide is predominantly an isomeric mixture of an alkyl group having the same number of carbon atoms.

6. The triaryl triazine ultraviolet light stabilizer composition of claim 1 wherein in said mixture are present at least 10% each of at least three different isomers of said —O-($C_6$ to $C_{12}$ alkyl) radical, wherein said isomers predominantly have the same number of carbon atoms.

7. A triaryl triazine ultraviolet light stabilizer composition comprising a mixture of compounds represented by the formula below:

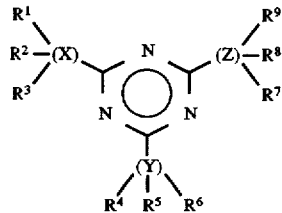

wherein independently for each of said compounds

X, Y, and Z are each the same or different aromatic carbocyclic radicals, and at least one of X, Y, and Z is substituted by a hydroxy group ortho to the point of attachment to the triazine ring, and at least one of $R^1$ to $R^9$ is an alkoxy radical of the formula —O-($C_6$ to $C_8$ alkyl) substituted at a point para to the point of attachment to the triazine ring, and the remainder of $R^1$ to $R^9$ are selected from the group consisting of hydrogen, hydroxy, alkyl, alkoxy, sulfonic, carboxy, halo, haloalkyl, and acylamino;

with the proviso that in said mixture are present at least 10% each of at least three different isomers of said —O-($C_6$ to $C_8$ alkyl) radical, wherein % is based on the total —O-($C_6$ to $C_8$ alkyl) radicals.

8. The triaryl triazine ultraviolet light stabilizer composition of claim 7 wherein for each said triaryl triazine compound:

(a) X, Y, and Z are each phenyl groups, (b) only one of X, Y, and Z is substituted by a hydroxy group ortho to the point of attachment to the triazine ring, (c) at least one —O-($C_6$ to $C_8$ alkyl) radical is substituted, on the same phenyl group as said hydroxy group, at a point para to the point of attachment of the phenyl group to the triazine ring, and (d) the remainder of the $R^1$, $R^2$, $R^3$, $R^4$, $R^5$, $R^6$, $R^7$, $R^8$, and $R^9$ are selected from the group consisting of hydrogen and alkyl groups.

9. The triaryl triazine ultraviolet light stabilizer composition of claim 7 wherein said at least three different —O-($C_6$ to $C_8$ alkyl) radicals are formed from a mixture of isomeric $C_6$ to $C_8$ alkyl halides containing at least 10% each of at least three different isomers.

10. The triaryl triazine ultraviolet light stabilizer composition of claim 9 wherein said at least three different-O-($C_6$ to $C_8$) alkyl radicals are formed from a mixed isomeric alkyl halide derived from "Oxo" process alcohols.

11. The triaryl triazine ultraviolet light stabilizer composition of claim 9 wherein the alkyl group of said alkyl halide is predominantly an isomeric mixture of an alkyl group having the same number of carbon atoms.

12. The triaryl triazine ultraviolet light stabilizer composition of claim 7 wherein in said mixture are present at least 10% each of at least three different isomers of said —O-($C_6$ to $C_8$ alkyl) radical, wherein said isomers predominantly have the same number of carbon atoms.

13. A triaryl triazine ultraviolet light stabilizer composition comprising a mixture of compounds represented by the formula below:

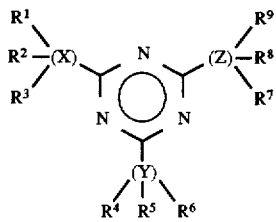

wherein independently for each of said compounds

X, Y, and Z are each the same or different aromatic carbocyclic radicals, and at least one of X, Y, and Z is substituted by a hydroxy group ortho to the point of attachment to the triazine ring, and at least one of $R^1$ to $R^9$ is an alkoxy radical of the formula —O-($C_6$ alkyl) substituted at a point para to the point of attachment to the triazine ring, and the remainder of $R^1$ to $R^9$ are selected from the group consisting of hydrogen, hydroxy, alkyl, alkoxy, sulfonic, carboxy, halo, haloalkyl, and acylamino;

with the proviso that in said mixture are present at least 10% each of at least three different isomers of said —O-($C_6$ alkyl) radical, wherein % is based on the total —O-($C_6$ alkyl) radicals.

14. The triaryl triazine ultraviolet light stabilizer composition of claim 13 wherein for each said triaryl triazine compound:

(a) X, Y, and Z are each phenyl groups, (b) only one of X, Y, and Z is substituted by a hydroxy group ortho to the point of attachment to the triazine ring, (c) at least one —O-($C_6$ alkyl) radical is substituted, on the same phenyl group as said hydroxy group, at a point para to the point of attachment of the phenyl group to the triazine ring, and (d) the remainder of the $R^1$, $R^2$, $R^3$, $R^4$, $R^5$, $R^6$, $R^7$, $R^8$, and $R^9$ are selected from the group consisting of hydrogen and alkyl groups.

15. The triaryl triazine ultraviolet light stabilizer composition of claim 14 wherein said at least three different —O-($C_6$ alkyl) radicals are formed from a mixture of isomeric $C_6$ alkyl halides containing at least 10% each of at least three different isomers.

16. The triaryl triazine ultraviolet light stabilizer composition of claim 15 wherein said at least three different-O-($C_6$ alkyl) radicals are formed from a mixed isomeric alkyl halide derived from "Oxo" process alcohols.

17. A triaryl triazine ultraviolet light stabilizer composition comprising a mixture of compounds represented by the formula below:

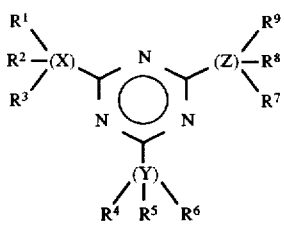

wherein independently for each of said compounds

X, Y, and Z are each the same or different aromatic carbocyclic radicals, and at least one of X, Y, and Z is substituted by a hydroxy group ortho to the point of attachment to the triazine ring, and at least one of $R^1$ to $R^9$ is an alkoxy radical of the formula —O-($C_8$ alkyl) substituted at a point para to the point of attachment to the triazine ring, and the remainder of $R^1$ to $R^9$ are selected from the group consisting of hydrogen, hydroxy, alkyl, alkoxy, sulfonic, carboxy, halo, haloalkyl, and acylamino;

with the proviso that in said mixture are present at least 10% each of at least three different isomers of said —O-($C_8$ alkyl) radical, wherein % is based on the total —O-($C_8$ alkyl) radicals.

18. The triaryl triazine ultraviolet light stabilizer composition of claim 17 wherein for each said triaryl triazine compound:

(a) X, Y, and Z are each phenyl groups, (b) only one of X, Y, and Z is substituted by a hydroxy group ortho to the point of attachment to the triazine ring, (c) at least one —O-($C_8$ alkyl) radical is substituted, on the same phenyl group as said hydroxy group, at a point para to the point of attachment of the phenyl group to the triazine ring, and (d) the remainder of the $R^1$, $R^2$, $R^3$, $R^4$, $R^5$, $R^6$, $R^7$, $R^8$, and $R^9$ are selected from the group consisting of hydrogen and alkyl groups.

19. The triaryl triazine ultraviolet light stabilizer composition of claim 17 wherein said at least three different —O-($C_8$ alkyl) radicals are formed from a mixture of isomeric $C_8$ alkyl halides containing at least 10% each of at least three different isomers.

20. The triaryl triazine ultraviolet light stabilizer composition of claim 19 wherein said at least three different-O-($C_8$ alkyl) radicals are formed from a mixed isomeric alkyl halide derived from "Oxo" process alcohols.

* * * * *